(12) United States Patent
Lu et al.

(10) Patent No.: US 9,198,593 B2
(45) Date of Patent: Dec. 1, 2015

(54) ELECTROCARDIOGRAM MONITORING

(71) Applicant: Physio-Control, Inc., Redmond, WA (US)

(72) Inventors: Zhong Qun Lu, Bothell, WA (US); Richard C. Nova, Kirkland, WA (US); Paul S. Tamura, Seattle, WA (US); Gary A. DeBardi, Kirkland, WA (US); David W. Tecklenburg, Mill Creek, WA (US); Tyler R. Hart, Kenmore, WA (US); James S. Neumiller, Redmond, WA (US); Richard J. Cardin, Duvall, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 45 days.

(21) Appl. No.: 13/650,570

(22) Filed: Oct. 12, 2012

(65) Prior Publication Data
US 2013/0041421 A1 Feb. 14, 2013

Related U.S. Application Data

(62) Division of application No. 11/679,154, filed on Feb. 26, 2007, now Pat. No. 8,315,693.

(60) Provisional application No. 60/777,308, filed on Feb. 28, 2006.

(51) Int. Cl.
*A61N 1/39* (2006.01)
*A61B 5/0424* (2006.01)
*A61B 5/00* (2006.01)

(52) U.S. Cl.
CPC ............. *A61B 5/0424* (2013.01); *A61B 5/6843* (2013.01); *A61B 5/7242* (2013.01); *A61N 1/3931* (2013.01)

(58) Field of Classification Search
CPC . A61N 1/3912; A61N 1/3962; A61N 1/3754; A61N 1/39; A61N 1/3625; A61N 2001/083; A61N 1/37; A61N 1/3937; A61N 1/046; A61N 1/3925; A61N 1/08; A61N 1/375; A61N 1/3752; A61N 1/048; A61N 1/36014; A61N 1/362; A61B 5/0424; A61B 2562/222; A61B 2562/227; A61B 2505/01; H01R 2201/12
USPC ............... 607/5–6, 9–10, 27, 36–38, 62, 115, 607/142; 600/372, 382, 508–509
See application file for complete search history.

(56) References Cited

U.S. PATENT DOCUMENTS

4,917,099 A    4/1990  Stice
5,020,541 A    6/1991  Marriott
(Continued)

*Primary Examiner* — Deborah Malamud
(74) *Attorney, Agent, or Firm* — Marger Johnson (57) ABSTRACT

Techniques for determining whether one or more leads are not adequately connected to a patient, e.g., for ECG monitoring, are described. The techniques involve injection of an integrated signal (which includes a test signal) into one lead, and monitoring the driven lead and the response at the other leads, including the common mode and the difference between the other leads. These "lead-off" detection techniques may be provided by an external defibrillator that provides three-wire ECG monitoring. Techniques for determining a type of a cable coupled to a defibrillator are also described. The cable-type identification may allow a defibrillator to, for example, operate in either a three-wire ECG monitoring mode or a therapy mode, based on whether a three-wire ECG cable or a defibrillation cable is coupled to the defibrillator.

8 Claims, 7 Drawing Sheets

(56) References Cited

U.S. PATENT DOCUMENTS

| | | |
|---|---|---|
| 5,233,986 A * | 8/1993 | Robson .......................... 607/28 |
| 5,431,684 A | 7/1995 | Archer et al. |
| 5,453,698 A | 9/1995 | Williams et al. |
| 5,549,646 A | 8/1996 | Katz et al. |
| 5,591,213 A | 1/1997 | Morgan |
| 5,632,280 A | 5/1997 | Leyde et al. |
| 5,902,249 A | 5/1999 | Lyster |

* cited by examiner

ELECTROCARDIOGRAM MONITORING

PRIORITY CLAIM

This application is a division of U.S. patent application Ser. No. 11/679,154, entitled "Electrocardiogram Monitoring," filed Feb. 26, 2007, currently pending, which claims the benefit of U.S. provisional application No. 60/777,308, entitled "Electrocardiogram Monitoring," filed on Feb. 28, 2006, both of which are hereby incorporated by reference in their entirety.

TECHNICAL FIELD

The invention relates to medical devices for treating cardiac conditions, and more particularly, to medical devices using an electrocardiogram.

BACKGROUND

In a typical implementation, the electrocardiogram (ECG) represents a difference in potential between two or more electrodes placed upon the body of the patient. Leads connect the electrodes to the inputs of a differential amplifier. The differential amplifier detects the ECG signals associated with the contraction of the heart and amplifies the ECG signals so that the ECG signals can be analyzed and/or displayed for analysis.

An external defibrillator, such as an automated external defibrillator (AED), is an example of a device that may analyze and/or display ECG signals. For example, based upon the ECG signals, an AED may assess whether a defibrillation shock is indicated, and charge an energy storage element in preparation for giving the shock. When a shock is indicated, the AED may cue the operator to administer the shock, or the AED may administer the shock automatically. The patient receives the shock through the same electrodes.

It is possible to reduce outside electrical noise associated with ECG signals by applying a third electrode to the patient and connecting the third electrode to a driven reference input of the common mode of the other two electrodes via a driven reference lead circuit. When noise is reduced, the ECG signals are generally easier to analyze. Consequently, as an example, an AED may be more capable of determining whether shock therapy is appropriate and what degree of therapy is appropriate. Further, noise reduction is particularly important in an ECG that is displayed for human analysis. For example, it is generally desirable that a displayed ECG be of "diagnostic quality," e.g., conform to the standards for diagnostic ECG devices relating to noise, artifacts, and the like, promulgated by the Association for the Advancement of Medical Instrumentation (AAMI).

Another factor that may influence the clarity of the ECG signal is the quality of the connection of the electrodes to the patient. In the case of a patient with a hairy chest, for example, an electrode placed on the chest may lose contact with the patient's skin, resulting in a poor electrical connection. An inadequate electrical connection for one or more electrodes may, for example, result in an inability to detect the ECG signal, or an ECG signal that is not of adequate quality for analysis.

SUMMARY

In general, the invention is directed to techniques for detecting whether the leads coupled to an ECG monitoring device, e.g., the three leads coupled to a three wire electrocardiogram monitoring device, are adequately connected to a patient. More particularly, an ECG monitoring device according to the invention injects an integrated signal via one of the leads, and determines whether one or more of the leads are not adequately connected based on the response at the other leads. The integrated signal includes a test signal and a common mode signal from the other, e.g., non-driven, leads. In some embodiments, the ECG monitoring device may advantageously be able to identify more specifically which one or more of the leads are not adequately connected.

If the ECG monitoring device determines that one or more leads are not adequately connected to the patient, the device may provide an indication to that effect to a user. The indication may be a general indication that one or more of the leads are not adequately connected. In other embodiments, the indication may more specifically direct the user's attention to a particular one or more leads. In either case, the indication may allow the user to address the inadequate connection such that an ECG of adequate quality may be detected.

The ECG monitoring device may include an integrator that integrates a test signal and a common mode signal from the other leads to generate an integrated signal. The ECG monitoring device may determine whether one or more leads are not adequately connected based on the integrated signal. For example, the ECG monitoring device may compare one or both of an AC amplitude and a DC offset of the integrated signal to respective thresholds. If the AC amplitude or DC offset exceeds the threshold, the device may indicate that either the lead driven with the integrated signal, all other leads, or all leads are not adequately connected.

The ECG monitoring device may also include a difference unit, which may be difference amplifier, that generates a difference signal as a function of signals detected via the non-driven leads. The device may determine whether one or more leads are not adequately connected based on the difference signal. For example, the device may compare the AC difference signal to a threshold, and determine that one of the non-driven leads is not adequately connected to the patient if the signal exceeds a threshold. In some embodiments, the device may determine which of the leads is off based on the phase of the difference signal.

An ECG monitoring device may take the form of an external defibrillator, such as an AED. The defibrillator may provide ECG monitoring and therapy delivery via a common set of three or more electrodes. In such embodiments, the defibrillator may monitor a driven, e.g., three-wire, ECG for the purpose of determining whether a defibrillation pulse should be delivered to a patient. Two or more of the leads may include electrodes with a larger surface area for delivery of defibrillation pulses or other electrical therapy.

In other embodiments, the defibrillator may be coupled to different cables, which provide either ECG electrodes or defibrillation electrodes, via a common receptacle of the defibrillator. Such embodiments may allow a user to use less expensive ECG monitoring electrodes if ECG monitoring of the patient is desired, reserving use of a defibrillation electrode and cable set for situations in which therapy will be delivered to the patient. The defibrillator may detect which type of cable is received by the receptacle, and select an operational mode based on the cable.

For example, the defibrillator may detect an ECG monitoring cable and enter an ECG monitoring mode in which delivery of therapy via the ECG electrodes is avoided. In the ECG monitoring mode, the defibrillator may begin driving one of the leads to provide a diagnostic quality ECG signal. The ECG monitoring mode may also include monitoring whether leads are adequately connected to a patient, as discussed above. If the defibrillator detects a therapy, i.e.; defibrillation cable, the defibrillator may enter a therapy mode in which the defibrillator operates as an AED or manual defibrillator, i.e., is able to deliver therapy via the leads.

The defibrillator may include a cable-type identification circuit, and at least one cable able to be used with the defibrillator may include a cable-type identification conductor separate from the patient therapy and monitoring leads. The cable-type identification conductor may short at least a portion of cable-type identification circuit, the defibrillator may detect the short to identify the type of the cable. The defibrillator may detect the presence or absence of the conductor, e.g., the presence or absence of a short, to identify which one of two cable-types is coupled to the defibrillator. In some embodiments, different configurations of the cable-type identification circuits may short different portions of the cable-type identification circuit, and the defibrillator may be able to identify more than two cable types based on the which one or more portions of the circuit are shorted.

For example, in some embodiments, the defibrillator may additionally detect a combined three-wire monitoring and therapy cable, i.e., with at least two defibrillation leads and an additional lead, which was discussed above. In response to detecting the combined cable, the defibrillator may enter an integrated three-wire monitoring and therapy mode that includes monitoring a 3-wire ECG via the leads, with one of the leads provided by the cable driven, and delivery of defibrillation therapy via the leads that include defibrillation electrodes. Further, in some embodiments, a defibrillator may additionally or alternatively detect cables intended for use with particular types of patients, such as cables intended for use with pediatric patients. In response to detecting such cables, the defibrillator may enter a different mode, or modify some aspect of therapy or monitoring in a way that is particularized for the patient. For example, in response to detecting a pediatric cable, the defibrillator may deliver, or recommend delivery of, defibrillation pulses with energy levels that are reduced relative to those for adult patients.

In one embodiment the invention is directed to a method comprising receiving a common mode signal via a first lead and a second lead coupled to an electrocardiogram monitoring device, integrating a test signal and the common mode signal to generate an integrated signal, and injecting the integrated signal into a third lead coupled to the electrocardiogram monitoring device. The method further comprising generating a difference signal based on a difference between a first signal obtained via the first lead and a second signal obtained via the second lead, and indicating whether any of the first lead, the second lead, and the third lead are not adequately connected to a patient based on the integrated signal and the difference signal.

In another embodiment, the invention is directed to an electrocardiogram monitoring device comprising an integrator that receives a common mode signal via a first lead and a second lead coupled to an electrocardiogram monitoring device, and integrates a test signal and the common mode signal to generate an integrated signal. The device further comprises a drive circuit that injects the integrated signal into a third lead coupled to the electrocardiogram monitoring device, and a difference unit that generates a difference signal based on a difference between a first signal obtained via the first lead and a second signal obtained via the second lead. The device further comprises a processor that indicates whether any of the first lead, the second lead, and the third lead are not adequately connected to a patient based on the integrated signal and the difference signal.

In another embodiment, the invention is directed to an electrocardiogram monitoring device comprising means for receiving a common mode signal via a first lead and a second lead coupled to an electrocardiogram monitoring device, means for integrating a test signal and the common mode signal to generate an integrated signal, means for injecting the integrated signal into the third lead coupled to the electrocardiogram monitoring device, means for generating a difference signal based on a difference between a first signal obtained via the first lead and a second signal obtained via the second lead, and means for indicating whether any of the first lead, the second lead, and the third lead are not adequately connected to a patient based on the integrated signal and the difference signal.

In another embodiment, the invention is directed to a system comprising an elongated external cable having a proximal end and a distal end, and an external defibrillator. The cable comprises a plurality of leads that extend from the proximal end to the distal end and convey electrical signals between a patient at the distal end and the proximal end, and a connector located at the proximal end that includes a cable-type identification conductor separate from the leads located on an external surface of the connector. The external defibrillator comprises circuitry that at least one of monitors or delivers therapy to the patient, a cable-type identification circuit, and a receptacle that receives the connector, couples the leads to the circuitry that at least one of monitors or delivers therapy to the patient, and couples the cable-type identification conductor to the cable type detection circuit. The cable-type identification conductor creates a short circuit in the cable-type identification circuit, and the external defibrillator detects the short circuit and identifies a type of the external cable based on the detection.

The invention may provide one or more advantages. For example, the invention may allow detection of whether one or more leads are not adequately connected to a patient for ECG monitoring. In some embodiments, the invention may advantageously allow identification of which one or more leads are not adequately connected.

Further, by identifying the type of cable coupled to a defibrillator, the defibrillator may be able to provide separate therapy and monitoring modes. Separate therapy and monitoring modes may allow lower cost ECG monitoring electrodes to be used monitoring, and avoid delivery of therapy via such electrodes. Further, the separate modes may allow the device to determine whether to perform therapy functions, e.g., automated evaluation of the ECG and recommendation of therapy, or monitoring functions, e.g., driving a monitoring lead and determining whether the leads are adequately connected to a patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
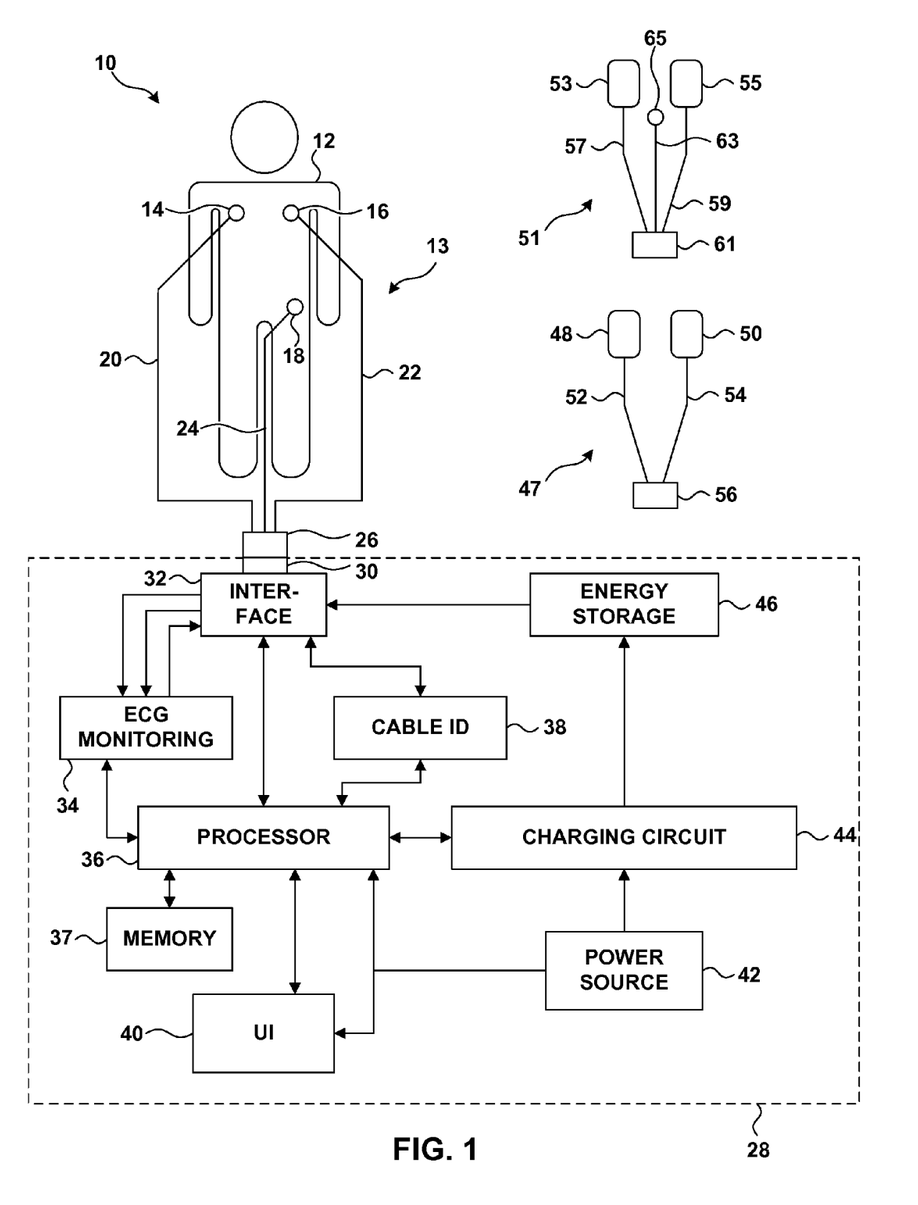
FIG. 1 is a block diagram illustrating an example system including defibrillator coupled to a patient by a three-wire ECG monitoring cable.

FIG. 1 is a block diagram illustrating an example system 10 including a defibrillator 28 coupled to a patient 12 by an elongated three-wire ECG monitoring cable 13. Cable 13 includes three leads 20, 22 and 24 that convey electrical signals between defibrillator 28 and patient 12. Cable 13 also includes or is coupled to three ECG monitoring electrodes 14, 16 and 18 at its distal end, i.e., leads 20, 22 and 24 are coupled to the electrodes at their distal ends. Electrodes 14, 16 and 18 may be adhesive electrodes pads, which may include a snap or other connection to the end of leads 20, 22 and 24, as is known in the art. At its proximal end, cable 13 includes a connector 26 that is received by a receptacle 30 of defibrillator 28 to physically and electrically couple the cable to the defibrillator.

As illustrated by FIG. 1, system 10 may also include an elongated defibrillator cable 47, which may be coupled to defibrillator 28 instead of ECG monitoring cable 13. Defibrillator cable 47 includes leads 52 and 54 that convey electrical signals between patient 12 and defibrillator 28, as well as electrode pads 48 and 50 at the distal end of leads 52 and 54. Electrode pads 48 and 50 may be adhesive defibrillation electrode pads known in the art. At its proximal end, cable 47 may include a connector 56 that is received by receptacle 30 to physically and electrically couple the cable to the defibrillator.

In addition to cables 13 and 47, system 10 may also include a combined three-wire monitoring and therapy cable 51, which includes leads 57 and 59 attached to electrode pads 53 and 55, respectively, to allow defibrillator 28 to convey electrical signals between patient 12 and the defibrillator. Electrode pads 53 and 55 may be substantially similar to electrode pads 48 and 50, and may be sized to facilitate delivery of high-energy defibrillation pulses to patient 12. In addition to delivery of defibrillation pulses, electrode pads 53 and 55 may facilitate detection of electrical signals within patient 12, e.g., ECG monitoring.

Combined cable 51 also includes a third lead 63 attached to a pad 65 so that defibrillator 28 may monitor a three-wire ECG with the therapy-monitoring cable. Pad 65 may have a smaller surface area suitable for ECG monitoring, but which may not be suitable for delivery of high-energy defibrillation pulses. Third lead 63 may, but does not necessarily, act as the driven lead during three-wire ECG monitoring. Combined cable 51 includes connector 61 at the proximal end of the cable. Combined cable 51 may allow defibrillator 28 to provide a third mode, where the defibrillator is capable of providing a defibrillation shock and a higher quality three-wire ECG without exchanging cables. In such embodiments, defibrillator 28 may analyze or allow a user to analyze the three-wire ECG to make therapy delivery decisions, and also deliver the therapy, via the combined cable 51.

Leads 20, 22 and 24 of cable 13, leads 52 and 54 of cable 47, and leads 57, 59 and 63 of cable 51, may be attached or otherwise bundled along a portion of the length of the cable, as is known in the art. Although illustrated in the context of a three-wire ECG monitoring cable 13 and a combined therapy-monitoring cable 51 with three leads, the invention may be used with cables including more than three leads.

In the illustrated embodiment, defibrillator 28 includes a cable identification circuit 38, through which a processor 36 identifies which type of cable, e.g., which of cables 13, 47, and 51 is coupled to defibrillator 28. Based on the identified type of cable, processor 36 may cause defibrillator 28 to operate in a selected one of a plurality of operational modes. For example, if processor 36 identifies ECG monitoring cable 13, processor 36 may cause defibrillator 28 to operate in an ECG monitoring mode. When defibrillator 28 is operating in the ECG monitoring mode, processor 36 may control an ECG monitoring module 34 to drive one of leads 20, 22 and 24, and receive the ECG signal via the other two leads.

When defibrillator 28 is operating in the ECG monitoring mode, processor 36 may also control ECG monitoring module 34 to detect whether one or more of the leads are not adequately connected to patient 12, as will be described in greater detail below. Further, when defibrillator 28 is operating in a therapy mode, processor 36 may control monitoring the ECG via the two leads of cable 47, and delivery of therapy via the leads of cable 47, as will be described in greater detail below. By identifying the type of cable and entering an appropriate mode, defibrillator 28 and processor 36 may, for example, avoid delivery of therapy to patient 12 via ECG monitoring cable 13, which may be harmful to the patient.

In addition, when defibrillator 28 is operating in a combined three-wire ECG and therapy mode with combined cable 51, processor 36 may control monitoring of a three-wire ECG via the leads 57, 59 and 63, and delivery defibrillation pulses via leads 57 and 59, without changing cable 51. In this manner, combined cable 51 may be more suitable for patients in critical care or having imminent cardiac problems. Processor 36 may control ECG monitoring module 34 to drive one of leads 57, 59 and 63, and receive the EGG signal via the other two leads. Processor 36 may use the three-wire ECG to decide whether defibrillation therapy should be delivered to the patient via leads 57 and 59 and electrodes 53 and 55.

Further, in some embodiments, when defibrillation therapy is delivered, processor 36 may disable or otherwise protect lead 63 e.g., by modifying switches within interface 32, to prevent delivery of defibrillation therapy via electrode 65. As discussed above, electrode 65 may have a smaller surface area than electrode pads 53 and 55 that may be unsuitable for delivery of high-energy defibrillation pulses. In the therapy-monitoring mode, defibrillator 28 may provide leads-off monitoring in the manner described below with reference to cable 13 and the ECG monitoring mode. However, the thresholds for such identification may be different in therapy-monitoring mode as compared to a dedicated ECG mode due to, for example, differences between electrodes 14, 16 and 18, and electrodes 53, 55 and 65.

Processor 36 may include any one or more of a microprocessor, digital signal processor (DSP), application specific integrated circuit (ASIC), field programmable gate array (FPGA), or other digital logic circuitry. A memory 37 may store instructions that, when executed by processor 36, cause processor 36 to provide the functionality ascribed to the processor and defibrillator 28 herein. Memory 37 may also store patient data gathered during treatment or monitoring of patient 12, as well as treatment or monitoring protocols, including defibrillation pulse energy level protocols or progressions, and thresholds and algorithms used to detect cardiac fibrillation. Memory 37 may also store the thresholds used to detect whether one or more leads of an ECG monitoring cable are not adequately detected to a patient, which will be described in greater detail below. Memory 37 may include, for example, any one or more of a random access memory (RAM), read only memory (ROM), non-volatile RAM (NVRAM), electronically erasable programmable ROM (EEPROM), or flash memory.

In addition to receptacle 30, cables 13, 47, and 51 are coupled to defibrillator by an interface 32. When defibrillator 28 is coupled to cable 47 and operating in a therapy mode, or coupled to cable 51 and operating in the combined mode, defibrillator 28 may sense electrical activity of the heart of patient 12 and deliver defibrillation pulses to patient 12 via electrodes 48 and 50 or 53 and 55. Interface 32 may include a switch (not shown in FIG. 2) that, when activated, couples an energy storage circuit 46 to the electrodes. Energy storage circuit 46 stores the energy to be delivered to patient 12 in the form of a defibrillation pulse. The switch may be of conventional design and may be formed, for example, of electrically operated relays. Alternatively, the switch may comprise an arrangement of solid-state devices such as silicon-controlled rectifiers or insulated gate bipolar transistors.

Energy storage circuit 46 includes components, such as one or more capacitors, that store the energy to be delivered to patient 12 via the electrodes. Before a defibrillation pulse may be delivered to patient 12, energy storage circuit 46 must be charged. Processor 36 directs a charging circuit 44 to charge energy storage circuit 46 to a high voltage level. Charging circuit 44 comprises, for example, a flyback charger that transfers energy from a power source 42 to energy storage circuit 46.

Defibrillator 28 may be a manual defibrillator or an AED. Where defibrillator 28 is a manual defibrillator, a caregiver using defibrillator 28 may select an energy level for each defibrillation pulse delivered to patient 12. Processor 36 may receive the selection made by the caregiver via a user interface 40, which may include input devices, such as a keypad and various buttons or dials, and output devices, such as various indicator lights, a cathode ray tube (CRT), light emitting diode (LED), or liquid crystal display (LCD) screen, and a speaker. In some embodiments, user interface 40 may include a touch sensitive display that acts both displays information to a user and receives user input. Where defibrillator 28 is an AED, processor 36 may select an energy level from a preprogrammed progression of energy levels stored in memory 37 based on the number of defibrillation pulses already delivered to patient 12.

When the energy stored in energy storage circuit 46 reaches the desired energy level, processor 36 controls user interface 40 to provide an indication to a user that defibrillator 28 is ready to deliver a defibrillation pulse to patient 12, such as an indicator light, displayed message, or a voice prompt. The defibrillation pulse may be delivered manually or automatically. Where the defibrillation pulse is delivered manually, the user may direct processor 36 to deliver the defibrillation pulse via user interface 40 by, for example pressing a button. In either case, processor 36 activates the switches of interface 32 to electrically connect energy storage circuit 46 to leads 52 and 54 and electrodes 48 and 50, or leads 57 and 59 and electrodes 53 and 55, and thereby deliver the defibrillation pulse to patient 12.

Processor 36 may modulate the defibrillation pulse delivered to patient 12. Processor 36 may, for example, control the switches of interface 32 to regulate the shape and width of the pulse. Processor 36 may control the switches to modulate the pulse to, for example, provide a multiphasic pulse, such as a biphasic truncated exponential pulse, as is known in the art.

Processor 36 may perform other functions as well, such as monitoring electrical activity of the heart of patient 12 sensed via electrodes. Processor 36 may determine whether the heart of patient 12 is fibrillating based upon the sensed electrical activity in order to determine whether a defibrillation pulse should be delivered to patient 12. Where a defibrillation pulse has already been delivered, processor 36 may evaluate the efficacy of the delivered defibrillation pulse by determining if the heart is still fibrillating in order to determine whether an additional defibrillation pulse is warranted. Processor 36 may automatically deliver defibrillation pulses based on these determinations, or may advise the caregiver of these determinations via user interface 40.

When defibrillator 28 is operating in the therapy mode, processor 36 may display an electrocardiogram (ECG) that reflects the electrical activity sensed via electrodes 48 and 50 via user interface 40. Because defibrillator 28 is operating in the therapy mode rather than the ECG monitoring mode when coupled to cable 47 or therapy-monitoring mode when coupled to cable 51, and therefore does not provide a driven lead, the displayed ECG may not be of as high a quality as a three-wire ECG. As mentioned above and discussed in greater detail below, processor may identify a type of cable, e.g., whether cable 13, 47, or 51 is attached, via a cable identification circuit 38, and enter either the therapy mode, an ECG monitoring mode, or a combined mode based on the identification.

Figure 2:
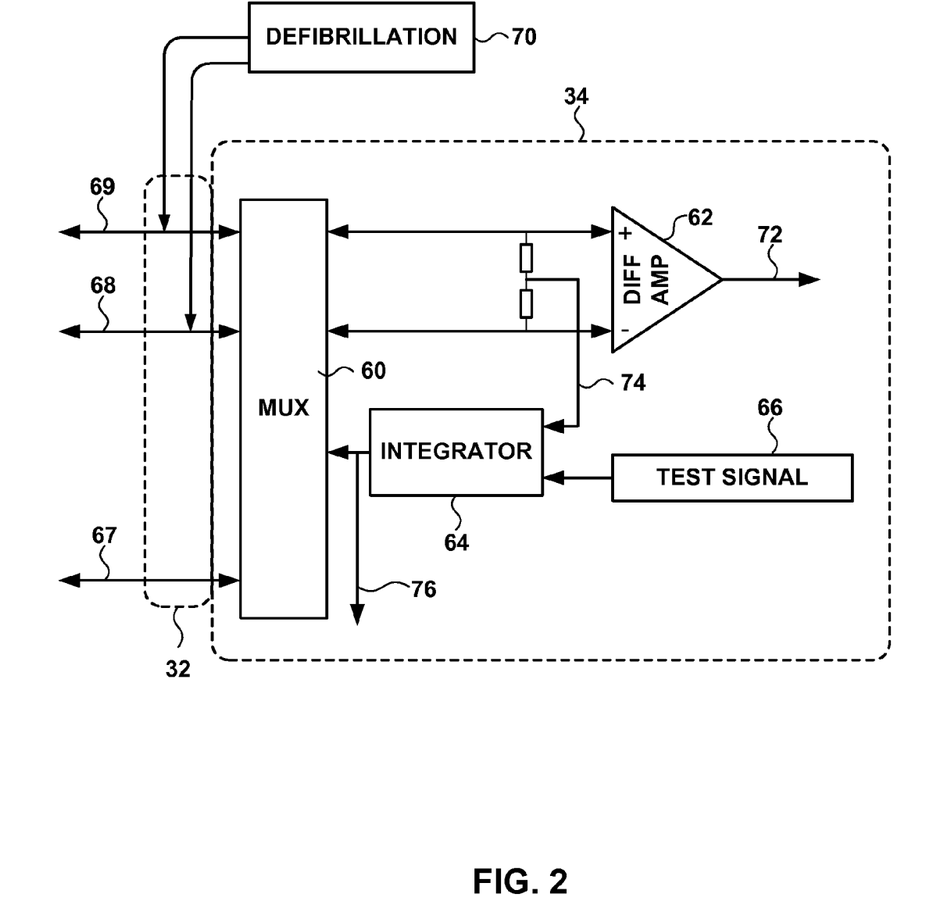
FIG. 2 is a block diagram illustrating an ECG monitoring circuit used to detect whether one or more leads of an ECG monitoring cable are not adequately connected to a patient.

FIG. 2 is a block diagram illustrating an ECG monitoring module 34. ECG monitoring module 34 may provide a driven lead to allow detection a higher-quality, three-wire ECG signal via the other leads of an ECG monitoring cable 13 or combined cable 51 (FIG. 1). ECG monitoring module 34 may also allow processor 36 (FIG. 1) to determine whether one or more of the leads are not adequately connected to patient 12. Processor 36 may control ECG monitoring module 34 to perform these functions when, for example, defibrillator 28 (FIG. 1) is operating in an ECG monitoring mode or a combined three-wire ECG and therapy mode.

As illustrated in FIG. 2, both ECG monitoring module 34 and a defibrillation module 70 are coupled to the leads of whichever of cables 13, 47, or 51 is coupled to defibrillator 28 by common channels 67-69 of interface 32. Interface 32 may include switches (not shown), and processor 36 may control the switches to control which of defibrillation module 70 and ECG monitoring module is coupled to channels 67-69 via the switches based on whether defibrillator 28 is in an ECG monitoring mode, a therapy mode, or a therapy-monitoring mode. In this manner, channels 68 and 69 are shared between ECG monitoring module 34 and a defibrillation module 70. Defibrillation module 70 may include charging circuit 44 and energy storage circuit 46 illustrated in FIG. 1.

When ECG monitoring module 34 is coupled to leads 20, 22 and 24 of cable 13 or coupled to leads 57, 59 and 63 of cable 51 by channels 67-69, processor 36 may control monitoring module 34 to drive one of the leads with a signal, and detect an ECG signal via the other two non-driven leads. More particularly, processor 36 may control an integrator 64 to generate an integrated signal 76 that drives one of the leads, and may receive the ECG based on a difference signal 72 generated by a difference unit, such as a difference amplifier 62, which is the difference between the signals detected by the other two leads. Although not shown in FIG. 2, ECG monitoring module 34 may include a variety of circuitry to condition difference signal 72 prior to delivery to processor 36 as an ECG, such analog or digital filters, amplifiers, and analog to digital conversion circuitry. For example, a band pass filter may filter difference signal 72 before the difference signal is sent to a processor. Processor 36 may display the ECG via a display of user interface 42 (FIG. 1).

The integrator 64 generates the integrated signal based on a common mode signal 74 of the non-driven leads. Common mode signal 74 provides negative feedback from the patient 12. In general, during ECG monitoring, integrated signal 76 acts to cancel at least lower frequency noise present in the common mode signal.

In the embodiment illustrated by FIG. 2, ECG monitoring module 34 includes a multiplexer 60. Processor 36 may control which of a plurality of leads is coupled to the output of integrator 64, e.g., which of the leads is the driven lead, and which of the leads are coupled to the inputs of differential amplifier 62 via multiplexer 60. In this manner, defibrillator 28 may display any of a Lead I, II or III ECG signal, as is known in the art. Processor 36 may receive selection of the Lead I, II or III ECG signal from a user via user interface 40, and configure the leads via multiplexer 60 according to the selection.

In other embodiments, ECG monitoring module 34 need not include multiplexer 60. In such embodiments, the connections between leads and the output of integrator 64 and inputs of differential amplifier 62, may be fixed. As an example, if lead 22 of cable 13 is connected to integrator 64 via channel 67, lead 24 is connected to the non-inverting (+) input of differential amplifier 62 via channel 69, and lead 20 is connected to the inverting (−) input of the differential amplifier via channel 68, the ECG derived from the signal output by the differential amplifier will be a Lead II ECG.

Processor 36 may also determine whether one or more of the leads are not adequately connected to the patient via ECG monitoring module 34. More particularly, processor 36 may control injection of a test signal 66 into integrator 64, which outputs an integrated signal to one of the leads, and determine whether one or more of the leads are not adequately connected to patient 12 based on the response detected at the non-driven leads and the driven lead 67.

As an example, the test signal 66 used to drive one of the leads may be a sinusoidal frequency at approximately 275 Hz. Test signal 66 may have a minor de bias. Although test signal 66 need not be sinusoidal in some embodiments, a sinusoidal test signal may advantageously reduce the electromagnetic interference from outside sources, and reduce the likelihood of charge buildup on the electrodes coupled to the patient, which may itself affect ECG signal quality. Further, test signal 66 may be at a frequency other than approximately 275 Hz. For example, test signal 66 may have any frequency between 150 Hz and 2 kHz. Test signal frequencies within this range may advantageously avoid interfering with the ECG signal, which primarily occurs below 150 Hz, and detection of implanted cardiac pacer activity, which general occurs above 2 kHz.

In general, if all of the leads are adequately connected to patient 12, test signal 66 will be small in amplitude at integrated signal 76 due to the cancellation from the integrated negative feedback. Test signal 66 is substantially absent from difference signal 72 because the test signal is a common mode signal simultaneously applied to both inputs of differential amplifier 62. If either the driven lead, or both of the non-driven leads, are not adequately connected to the patient, test signal 66, which is the 275 Hz sine wave in the above example, will be more significantly present in integrated signal 76. The elevated 275 Hz test signal 66 will exceed a pre-set threshold that indicates that the leads are not adequately connected to patient 12, i.e. the "leads-off" indication. If common-mode signal 74 does not include test signal 66, and therefore does not provide negative feedback from patient 12 to integrator 64 that includes test signal 66, the peak-to-peak amplitude and absolute value of the DC offset of the 275 Hz test signal within integrated signal 76 output by integrator 64 may increase relative to the input test signal 66. Accordingly, processor 36 may compare an amplitude, which may be the peak-to-peak amplitude, and/or the DC offset, i.e., the absolute value of the DC offset, of test signal 66 within integrated signal 76 to a threshold. Processor 36 may indicate that one or more leads are not adequately connected to patient 12 if the threshold is exceeded. Processor 36 may provide a general "leads-off" indication, or may more particularly indicate that either the driven lead, both of the non-driven leads, or all of the leads 20-24 are not adequately connected to patient 12, if the threshold is exceeded. Detecting the presence, absence, or strength of test signal 66 in common-mode signal 74 by monitoring integrated signal 76 is one way in which processor 36 may monitor the response at the non-driven leads to injection of test signal 66 at the driven lead.

Another way in which the processor may monitor the response to the test signal to detect whether one or more leads are not adequately connected is to monitor difference signal 72, which is generated by differential amplifier 62 based on the signals received from the non-driven leads. In general, if both of the non-driven leads connected to the inputs of differential amplifier 62 are adequately connected to patient 12, test signal 66 will be substantially absent from difference signal 72. However, if one of the non-driven leads is not adequately connected to the patient, the test signal will be present in the differential signal. Accordingly, processor 36 may compare the amplitude of difference signal to a threshold, and indicate that one or more leads are not adequately connected to patient 12 if the threshold is exceeded. Processor 36 may provide a general "leads-off" indication, or may more particularly indicate which of the non-driven leads is not adequately connected to patient 12, if the threshold is exceeded.

Further, in some embodiments, processor 36 may determine which of the non-driven leads is not adequately connected based on the phase of difference signal 72. For example, because integrator 64 includes an inverter, if processor 36 determines that difference signal 72 is substantially in phase with test signal 66, processor 36 may determine that the lead coupled to the non-inverting (+) input of difference amplifier 62 is not adequately connected to patient 12. If processor 36 determines that difference signal 72 is substantially out of phase with test signal 66, processor 36 may determine that the lead coupled to the inverting (−) input of difference amplifier 62 is not adequately connected to patient 12. In such embodiments, processor 36 may advantageous identify to a user which of the non-driven leads is not adequately connected to patient 12. Whether a general or more specific in the manner described above, processor 36 may indicate whether one or more leads are not adequately connected to patient 12 via user interface 42 of defibrillator 28, e.g., via a display, speaker, or one or more indicator lights.

Figure 3:
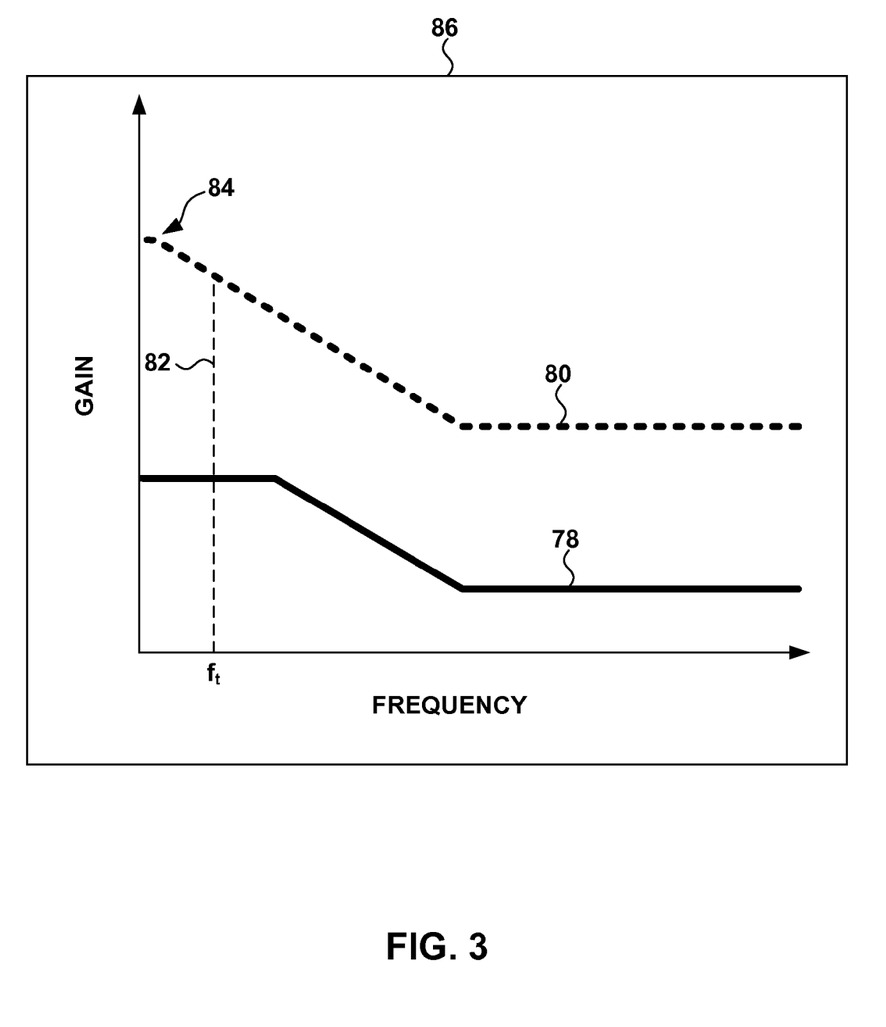
FIG. 3 is a bode plot illustrating a response of the ECG monitoring circuit to one or more leads not being adequately connected to the patient.

FIG. 3 is a bode plot 86 illustrating a response of ECG monitoring circuit 34 to one or more of leads 20, 22 and 24 not being adequately connected to patient 12. More particularly, bode plot 86 illustrates a closed-loop gain 78 of integrated signal 76 relative to test signal 66, corresponding to a condition all of the leads are adequately connected, and an open-loop gain 80 of the integrated signal relative to the test signal, corresponding to a condition either the driving lead or both non-driven leads are completely disconnected, as a function of frequency. As illustrated by bode plot 86, open-loop gain 80 is greater than closed-loop gain 78 across a relatively large range of frequencies, and particularly so around the frequency of the injected test signal 66 and at DC 84. Accordingly, processor 36 may monitor the amplitude of integrated signal 76 at approximately the test frequency signal and/or DC, e.g., the DC gain to detect whether one or more leads are not adequately connected to patient 12. When the leads are not adequately connected, the loop gain will generally fall between the boundaries of 78 and 80. A leads-off threshold can be specified, based on clinic preference, within the range defined by these two boundaries.

Figure 4:
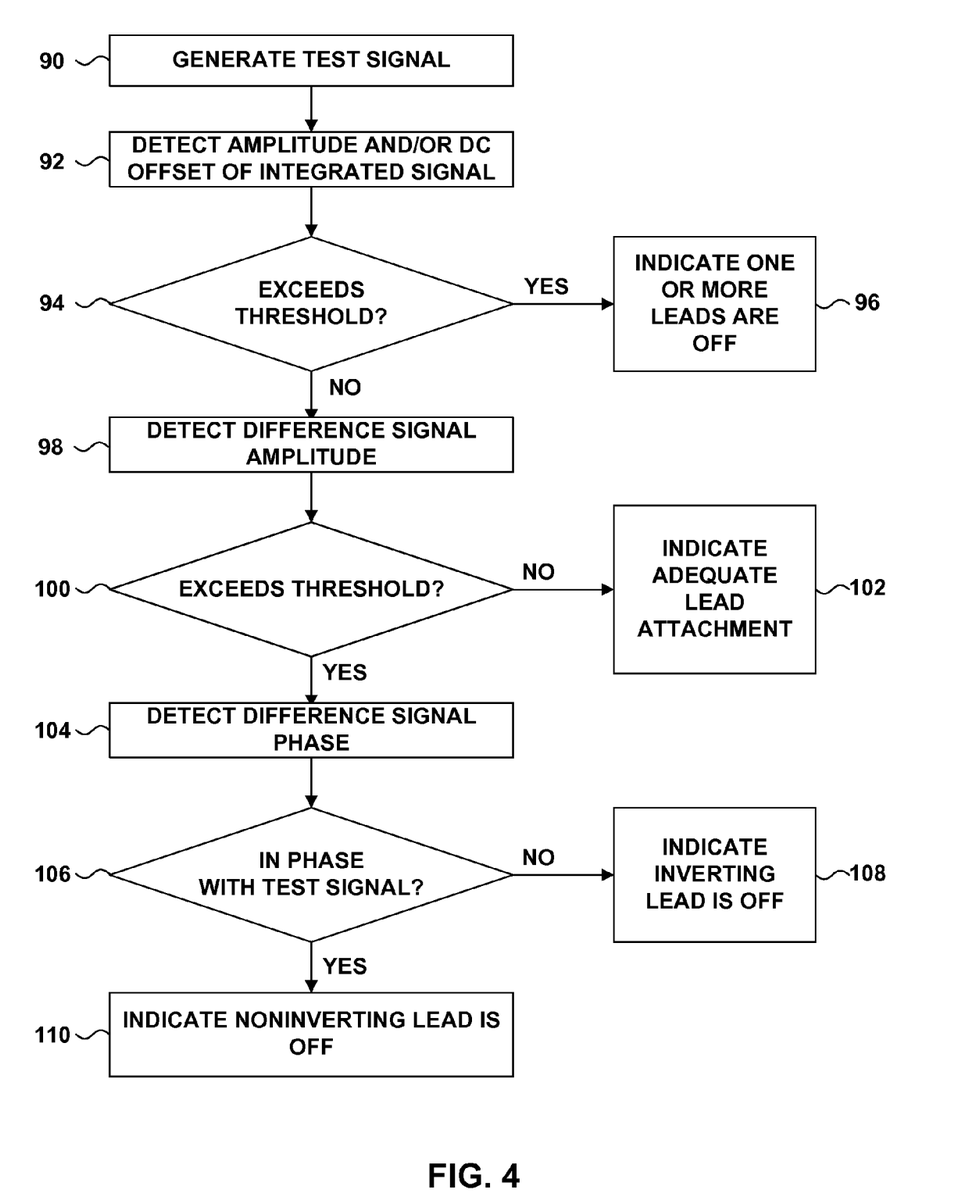
FIG. 4 is a flow diagram illustrating an example technique for determining whether one or more leads are not adequately connected to a patient.

FIG. 4 is a flow diagram illustrating an example technique for determining whether one or more of leads are not adequately connected to a patient. The illustrated technique may be performed by a defibrillator as controlled by a processor thereof. The illustrated technique may be performed by, for example, defibrillator 28 and processor 36 as described above with reference to FIGS. 1-3.

According to the example technique, processor 36 controls generation of a test signal 66 (90). An integrator 64 generates an integrated signal 76 based on a common-mode signal 74 from non-driven leads and the test signal, and injects the integrated signal into a driven one of the leads. Processor 36 detects at least one of an amplitude or DC offset of the integrated signal 76 (92). Processor 36 compares the amplitude or DC offset, e.g., the peak-to-peak amplitude or absolute value of the DC offset, to a threshold (94). If the threshold is exceeded, processor 36 provides an indication to a user via user interface 40 that one or more of the leads are not adequately connected to patient 12 (96). In some embodiments, the processor provides a more specific indication that the driven lead, both non-driven leads, or all leads are not adequately connected if the amplitude or DC offset of the integrated signal exceeds the threshold.

If the amplitude or DC offset does not exceed the threshold, processor 36 detects an amplitude of a difference signal 72 generated by a difference unit, e.g., a difference amplifier 62, based on signals detected by the non-driven leads (98). Processor 36 compares the amplitude to a threshold (100). If the amplitude of the difference signal does not exceed the threshold, processor 36 may provide an indication of adequate lead attachment e.g., "leads on," via user interface 42 (102). In other embodiments, processor 36 may provide no indication if the leads are adequately attached, i.e., may only provide lead attachment related indications if one or more leads are not adequately attached to patient 12.

If the amplitude of difference signal 72 exceeds the threshold, processor 36 may indicate that a lead is not adequately connected to patient 12, or may more specifically indicate that one of the non-driven leads is not adequately connected. In other embodiments, as illustrated in FIG. 4, processor 36 may detect the phase of the difference signal relative to the test signal if its amplitude exceeds the threshold (104). If difference signal 72 is substantially out of phase with test signal 66, processor 36 may indicate that the lead coupled to the inverting input of the difference unit is not adequately connected to patient 12 (108). If difference signal 72 is substantially in phase with test signal 66, processor 36 may indicate that the lead coupled to the noninverting input of the difference unit is not adequately connected to patient 12 (110).

Figure 5A:
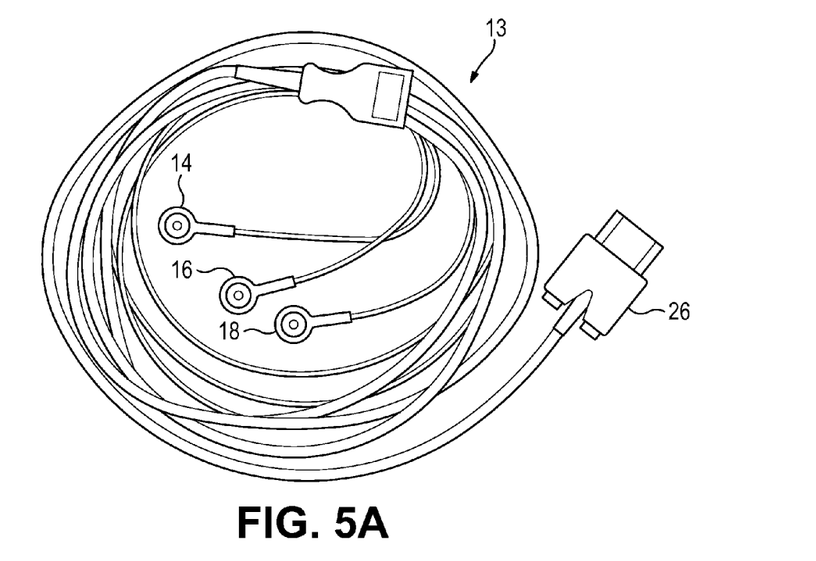
FIG. 5A is a view illustrating a three-wire ECG monitoring cable.

FIG. 5A shows three-wire electrocardiogram (ECG) cable 13. ECG cable 13 includes electrodes 14, 16 and 18 connected to the distal ends of leads 20, 22 and 24, respectively. Leads 20, 22 and 24 are combined into one insulated bundle at some location along cable 13 and couple to connector 26 at the proximal ends. Connector 26 provides an electrical contact interface to defibrillator 28.

Electrode 18 may be attached to the left leg of patient 12, electrode 16 may be attached to the left arm of the patient and electrode 14 may be attached to the right arm of the patient. The exact positioning of each electrode 14, 16 or 18 may slightly alter the ECG signal detected by defibrillator 28, but the altered signal may still adequately detect the ECG of patient 12. However, defibrillator 28 may detect if one of electrodes 14, 16 or 18 does not make adequately contact to the skin of patient 12, as described herein.

Figure 5B:
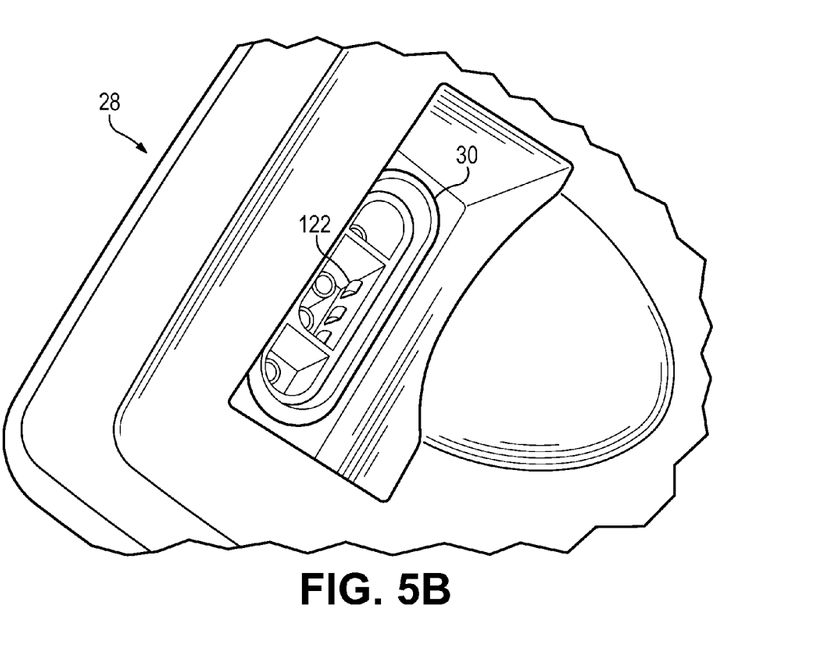
FIG. 5B is a view illustrating a portion of an example external defibrillator.

ECG cable 13 may be electrically coupled to defibrillator 28 through receptacle 30 shown in FIG. 5B, e.g., by receipt of connector 26 into receptacle 30. Receptacle 30 may be located at an easily accessed location of defibrillator 28 and provide multiple contacts with connector 26. In addition, receptacle 30 may accept the connectors of other external cables, such as connector 56 of defibrillator cable 47 or connector 61 of therapy-monitoring cable 51 of FIG. 1. Defibrillator 28 may automatically identify which external cable is plugged into receptacle 30 by detecting a cable-type identification conductor on the external surface of the connector via conductor contacts 122 located within receptacle 30. Three conductor contacts are shown in the example receptacle 30 so that defibrillator 28 can identify up to four different cables. In this manner, defibrillator 28 may be operated based upon the external cable plugged into receptacle 30. Conductor contacts 122 are three electrically conductive surfaces that are selectively coupled to each other via the electrically conductive cable-type identification conductor. Other embodiments of receptacle 30 may include more than three conductor contacts 122 to identify more than four difference cables.

Receptacle 30 is shown as an oval shaped structure within a rectangular recession. In other embodiments, receptacle may include other shapes, such as a circle, triangle, trapezoid, or other polygon. Alternatively, receptacle 30 may have an unsymmetrical shape that only accepts the connector of an external cable in a particular orientation. In addition, receptacle 30 may include a locking mechanism which prevents a connector from being removed from the receptacle accidentally. The locking mechanism may include a latch, a pin, a spring loaded lever, one or more mating indents and detents, or a friction fit.

Figure 6:
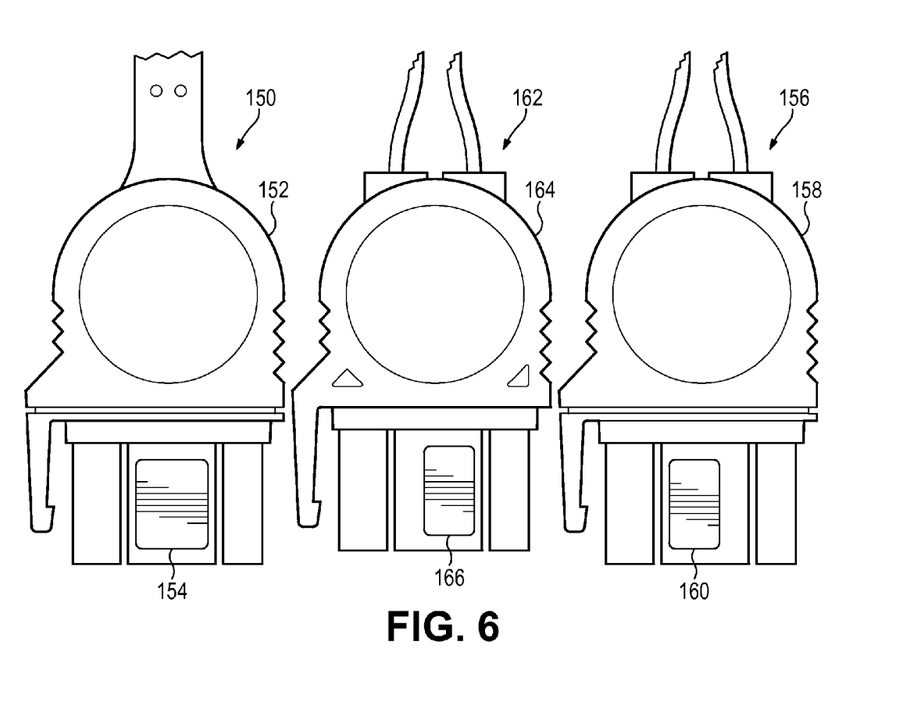
FIG. 6 is a perspective view illustrating a plurality of connectors of a plurality of cables.

FIG. 6 is a perspective view illustrating example embodiments of connectors for cables described herein, such as connectors 26, 56 and 61 of cables 13, 47 and 51. For example, connectors 150 and 158 may be attached to cables 13 and 47, respectively, while connector 162 is attached to another cable, such as a pediatric defibrillation cable. Connector 150 includes connector housing 152 and cable-type identification conductor 154 located at a proximal end of the connector along one external surface of the housing. Connector 156 includes connector housing 158 and cable-type identification conductor 160 located at a proximal end of the connector along one external surface of the housing. Connector 162 includes connector housing 164 and cable-type identification conductor 166 located at a proximal end of the connector along one external surface of the housing. Connector housings 152, 158 and 164 may be shaped to partially fit into receptacle 30 of FIG. 5B and to allow a user to hold each housing such that the user may easily insert the respective connector into the receptacle.

Conductors 154, 160 and 166 are each configured to allow defibrillator 28 to identify the "type" of their respect cables as such without input from a user. Conductors 154, 160 and 166 may be constructed of an electrically conductive metal plate or non-conductive metal or molded plastic coated with a conductive paint or coating. Alternatively, the conductors may be formed on the connectors by any one or more of a variety of processes, including vapor-deposition, sputter coating, lithography, or etching. Conductors 154, 160 and 166 may be of a shape or size such that it interacts with a cable-type identification circuit of defibrillator 28, e.g., shorts at least a portion of the circuit. Processor 36 of defibrillator 28 may identify the coupled cable, i.e., ECG monitoring cable 13, defibrillation cable 47, therapy-monitoring cable 51, or other type of cable, based on the interaction. For example, conductor 160 may touch two of three of electrical contacts, where one of the two electrical contacts provides a path to ground. Other cables may be identified by processor 36 through the use of a different conductor configuration, as shown in FIG. 6 by conductor 154 that touches all three contacts and conductor 166 that touches two other contacts, or the absence of a conductor. In this manner, processor 36 may cause defibrillator 28 to enter a mode of operation appropriate for the connected cable type, e.g., enter an ECG monitoring mode when coupled to an ECG monitoring cable, such as ECG cable 13.

Conductors 154, 160 and 166 are located on an external surface of connector housings 152, 158 and 162, respectively. In some embodiments, the external surface may be parallel or orthogonal to the direction in which a connector housing is inserted in receptacle 30. Conductors 154, 160 and 166 mate to one or more conductive surfaces within receptacle 30, however neither the conductive surfaces surround a portion of the conductor, nor does the conductor surround the conductive surface, i.e., a male to female type of connection. For example, conductor 154 is a substantially flat electrically conductive surface normal to the direction of connector housing 152 insertion, where the conductor surface mates to three substantially flat connector contacts 122 within receptacle 30 coupled to the cable-type identification circuit of defibrillator 28.

Figure 7:
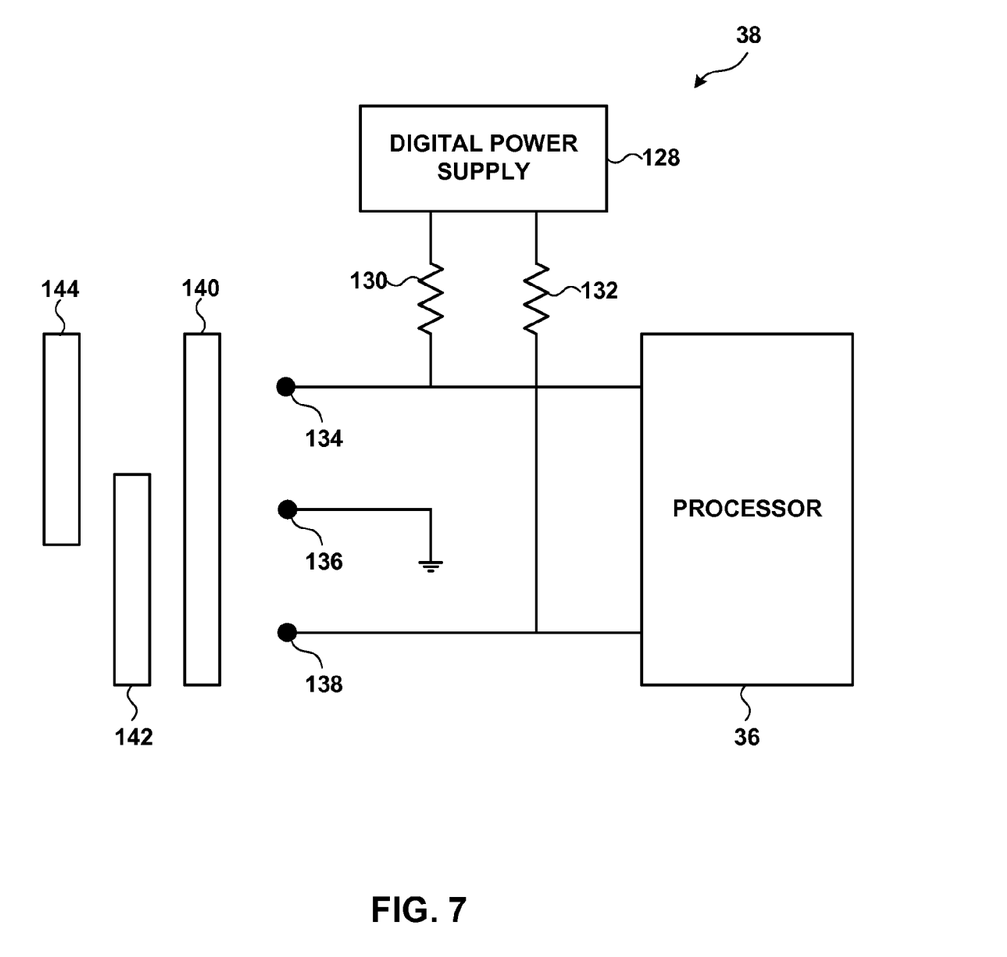
FIG. 7 is a block diagram illustrating example cable-type identification conductors and an example cable-type identification circuit which may be included in an external defibrillator.

FIG. 7 is a block diagram illustrating example cable-type identification conductors, and an example configuration of cable-type identification circuit 38. A digital power supply 128 delivers a logic signal to one or more inputs of processor 36 via one or more respective pull-up resistors 130 and 132. Conductors 140, 142 and 144 are example conductors which are configured, e.g., sized, to interact with one or both of contacts 134 and 138 coupled to the processor inputs and the digital power supply via the pull-up resistors, in addition to contact 136 that provides a path to ground. By interacting with such combinations of contacts 134, 136 and 138, the conductors short a selected one or more of the circuits providing a logic signal to processor 36 to change the logic state presented to one or more inputs of the processor, e.g., from high or one, to low or zero.

In the case of no conductor connecting any of the contacts 134, 136 and 138, processor 36 may receive a high voltage at both inputs. Conductor 144 is configured to interact with contacts 134 and 136, thereby connecting a first input of processor 36 to ground and driving it to a low voltage, while a second input other remains high. Conductor 142 interacts with contacts 138 and 136 to provide the opposite effect, i.e., the second input is connected to ground and driven low while the first input remains high. Conductor 140 interacts with all of the contacts to couple both inputs to ground, and thereby drive both inputs low.

Processor 36 may determine which cable-type identification conductor is present based upon one or more detected logic states, thereby identifying which external cable is connected to receptacle 30. In the configuration of cable-type identification circuit 38 illustrated by FIG. 7, as many as four different cable-types may be identified, i.e., one for each conductor configuration, and one for the absence of a conductor. A greater number of inputs to processor 36 may be used to detect many more different cable types by selectively coupling certain inputs. Based on a determination that no conductor is present, processor 36 may identify an associated type of cable, or determine that no cable is attached to defibrillator 28.

As discussed above, processor 36 may cause defibrillator to enter one of a plurality of operational modes based on the detected cable type. For example, processor 36 may cause defibrillator 28 to enter an ECG monitoring mode based on detection of cable 13, or a therapy mode based on detection of cable 47. Alternatively, processor 36 may cause defibrillator 28 to enter a combined three-wire ECG monitoring and therapy mode based upon detection of cable 51. Further, in some embodiments, once processor 36 identifies the cable type, processor 36 may provide an indication of the cable type to a user via user interface 40, e.g., via one or more indicator LEDs or a display. In this manner the user may verify that the attached cable is actually the cable the user desires to use with defibrillator 28.

Various embodiments have been described. However, one of ordinary skill in the art will understand that various modifications may be made to the described embodiments without departing from the scope of the invention. For example, the "circuits," "circuitry," "modules," "units" and the like described herein may be embodied as hardware, software, or any combination thereof.

Further, although described herein as allowing identification of either an ECG monitoring cable or a therapy cable for determining whether to enter a ECG monitoring mode, a therapy mode, or a combined mode, in other embodiments cable-type identification circuitry and cable-type identification conductors may be used to distinguish other types of cables used with an external defibrillator for other purposes. For example, processor of a defibrillator may adjust the delivery of the therapy to a patient based upon the identified external cable. The processor may identify, as an example, a pediatric cable attached to the defibrillator, and utilize a pediatric defibrillation mode designed for providing defibrillation to small children, e.g., deliver lower energy defibrillation pulses.

In other embodiments, the circuits and other hardware described to carry out certain aspects of the disclosure may be recreated with software. The software may be instructions stored on a computer readable medium that cause a processor to perform various tasks as described herein. For example, the computer readable medium may include instructions that cause a processor to provide a "leads-off" indication when one or more leads are not adequately attached to patient 12. Therefore, it is contemplated to translate the circuitry described herein into a computer readable medium that a processor uses to perform the functions described above.

Additionally, although described in the context of a three-wire ECG monitoring a defibrillator, the techniques for detecting whether leads are adequately connected to a patient may be used in any ECG monitoring device coupled to any number of leads. These and other embodiments are within the scope of the following claims.

The invention claimed is:
1. A system, comprising:
an elongated external cable having a proximal end and a distal end, the cable comprising:
a plurality of leads that extend from the proximal end to the distal end and are configured to convey electrical signals between the distal end and the proximal end, and a connector located at the proximal end that includes a cable-type identification conductor separate from the leads; and an external defibrillator comprising:
  circuitry configured to at least one of monitor or deliver therapy to the patient,
  a cable-type identification circuit located on an external surface of the connector, and
  a receptacle that is configured to receive the connector, is configured to couple the leads to the circuitry that is configured to at least one of monitor or deliver therapy to the patient, and is configured to couple the cable-type identification conductor to the cable type detection circuit, wherein the cable-type identification conductor is configured to create a short circuit in the cable-type identification circuit, and the external defibrillator is configured to detect the short circuit and identify a type of the external cable based on the detection, the external defibrillator further configured to adjust delivery of therapy to the patient based on the identified type of cable and to determine whether the patient is a pediatric patient based on the identified type of cable.

2. The system of claim 1, wherein the external defibrillator is configured to operate in one of a plurality of operational modes based on the identified type of the external cable.

3. The system of claim 2, wherein the external defibrillator is configured to operate in one of a therapy delivery mode or an electrocardiogram monitoring mode based on the identified type of the cable.

4. The system of claim 2, wherein the external cable comprises an electrocardiogram cable, and the defibrillator is configured to identify the cable as an electrocardiogram cable and is configured to operate in an electrocardiogram monitoring mode based on the identification.

5. The system of claim 2, wherein the external cable comprises a combined three-wire monitoring and therapy cable that includes at least three leads and at least two defibrillation electrodes, and the defibrillator is configured to identify the cable as the integrated three-wire monitoring and therapy cable and operate in an integrated three-wire monitoring and therapy mode based on the identification.

6. The system of claim 1, wherein the defibrillator is configured to adjust a defibrillation pulse energy level based on the identified type of the cable.

7. The system of claim 1, wherein the cable-type identification circuit includes a processor with at least two inputs,
  wherein the short circuit created by the cable-type identification conductor modifies the logic state of at least one of the inputs, and
  wherein the defibrillator is configured to identify at least four cable types based on modification of the at least one logic state.

8. The system of claim 1, wherein the cable-type identification conductor is located on an external surface of the connector.

* * * * *